United States Patent [19]

Onishi et al.

[11] 4,336,205
[45] Jun. 22, 1982

[54] METHOD FOR PRODUCING AROMATIC NITRILES

[75] Inventors: Isatsugu Onishi, Ikeda; Itsuo Furuoya, Suita; Ichiro Minato, Kobe, all of Japan

[73] Assignee: Takeda Chemical Industries, Ltd., Osaka, Japan

[21] Appl. No.: 249,461

[22] Filed: Mar. 31, 1981

[30] Foreign Application Priority Data

Apr. 1, 1980 [JP] Japan .................................. 55-43119

[51] Int. Cl.³ .................. C07C 120/14; C07D 213/57
[52] U.S. Cl. ................................. 260/465 C; 252/467; 546/286
[58] Field of Search ..................... 260/465 C; 252/467; 546/286

[56] References Cited

U.S. PATENT DOCUMENTS 3,497,545  2/1970  Golden et al. ................... 260/465 C
3,927,007  12/1975  Lüssling et al. ................. 260/465 C

FOREIGN PATENT DOCUMENTS 632702  5/1963  Belgium .
1114898  5/1968  United Kingdom .
1229283  4/1971  United Kingdom .
1246108  9/1971  United Kingdom .
1280326  7/1972  United Kingdom .

OTHER PUBLICATIONS

Japanese Published Unexamined Patent Application laid-open as No. 17360/1980.

*Primary Examiner*—Dolph H. Torrence
*Attorney, Agent, or Firm*—Wenderoth, Lind & Ponack

[57] ABSTRACT

Aromatic nitriles can be produced in high yields by ammoxidation of an alkyl-substituted aromatic compound in the presence of a catalyst containing oxides of (1) vanadium, (2) antimony and (3) at least one of uranium and chromium, even when concentration of the starting aromatic compound in the starting gas is high or mixing ratio of ammonia to the starting aromatic compound is reduced to the neighborhood of the stoichiometric equivalent.

9 Claims, No Drawings

METHOD FOR PRODUCING AROMATIC NITRILES

The catalysts which have been so far proposed for the ammoxidation of alkyl-substituted aromatic compounds to produce aromatic nitriles include for example two-component catalysts such as those based on vanadium oxide and chromium oxide (Belgium Patent No. 632,702) and on oxides of antimony and vanadium (British Patent No. 1114898), as well as oxides of vanadium and chromium being incorporated with oxides of manganese, molybdenum, boron or cobalt (British Patent No. 1246108), uranium (Japanese Published Unexamined Patent Application laid-open as No. 17360/'80), oxides of vanadium and antimony being incorporated with oxides of alkali metal and tungsten (British Patent No. 1229283), tungsten (British Patent No. 1280326), etc., and the like.

Nevertheless, the catalysts mentioned above involve many problems left unsolved from a standpoint of industrial production such as necessity of using ammonia in fairly large excess of the stoichiometric quantity, reduced yields of aromatic nitriles and difficulty in temperature control of catalyst beds. Particularly in the case of operation for reaction using a conventional multi-tube fixed catalyst bed, reaction of aromatic compounds having many alkyl-substituents at relatively high concentrations makes it difficult to control the temperature of the catalyst bed and therefore increases, in some instance, the temperature of the catalyst bed up to 600° to 1000° C. or higher levels, resulting in extreme reduction in nitrile yields and simultaneously drastic deterioration of the catalytic activity. Because of the fact, it has become inevitable to carry out operation for reaction using the multi-tube fixed catalyst bed at decreased concentrations of aromatic compounds or to conduct operation for reaction using a fluidized catalyst bed in which removal of reaction heat is easier than in the fixed bed. In such cases, however, lowering the concentration of aromatic compounds to such a level as may permit temperature control reduces space time yieldes, while, in the operation of the fluidized bed, space time yields are also reduced due to channeling and back-mixing of the reaction gas, and there remains several problems from a standpoint of commercial production such as deterioration of the catalyst due to abrasion thereof.

In view of the above, the present inventors conducted extensive research with a specific view to improving such disadvantages and, as a result, have succeeded in solving the above-mentioned problems by using as catalyst compositions containing oxides derived from (1) vanadium, (2) antimony and (3) at least one of uranium and chromium.

Thus, the present invention relates to a method for producing aromatic nitriles which comprises reacting an alkyl-substituted aromatic compound with ammonia and oxygen in the presence of a catalyst containing, as the active components, oxides of (1) vanadium, (2) antimony and (3) at least one of uranium and chromium.

The catalyst, which is useful in the present invention, has, as the active components, compound oxides or mixed oxides of the elements shown under the abovementioned oxides of (1), (2) and (3), whereby these are normally used in the state of being supported on a carrier. The catalyst, which is useful in the present invention, is obtainable by the per se known method of preparing solid catalysts, and, for example, can be prepared by the following procedure.

That is to say, the catalyst can be prepared by dissolving a vanadium-containing compound, antimony-containing compound and uranium- and chromium-containing compound being convertible into oxides through chemical reaction or heating in a suitable solvent such as water, alcohol, acid and alkali, then impregnating them into, or precipitating them on a carrier, and calcining for example at 300° to 800° C.

The above-mentioned vanadium-containing compound includes vanadium oxides (e.g. $V_2O_5$, $V_2O_4$, $V_2O_3$, etc.), vanadates (e.g. ammonium vanadate, vanadyl oxalate, vanadyl sulfate, vanadyl tartrate, etc.), and the like; as the antimony-containing compound there may be mentioned antimony oxides (e.g. $Sb_2O_3$, $Sb_2O_4$, $Sb_2O_5$, etc.), antimonic acids (e.g. orthoantimonic acid, metaantimonic acid, etc.), antimony halides and their partial hydrolyzates (e.g. $SbCl_3$, $SbCl_5$, $SbBr_3$, antimony oxychloride, etc.), organic antimony compounds (e.g. antimony triisopropoxide, etc.), antimony salts (e.g. antimony sulfide, antimony nitrate, antimony potassium tartrate, etc.), antimonates (e.g. potassium antimonate, etc.), and others; the uranium-containing compound includes uranium oxides (e.g. $UO_2$, $U_3O_8$, $UO_3$, etc.), uranyl nitrate, uranyl acetate, uranyl chloride, etc., and the chromium-containing compound is chromium oxides (e.g. CrO, $Cr_2O_3$, $CrO_3$, etc.), ammonium chromate, chromium slats (chromium nitrate, chromium chloride, chromium oxalate, chromium tartrate, chromium sulfate, etc.), etc.; these can be all led easily into oxides.

A formulating ratio for these vanadium-containing compound, antimony-containing compound and uranium- and chromium-containing compound is, per atom of vanadium, 0.1 to 10 of antimony, preferably 0.5 to 5, more preferably 1.0 to 3.0, and 0.01 to 5.0 of uranium, chromium, preferably 0.01 to 2.0, more preferably 0.02 to 1.0.

As the above-mentioned carrier, use is preferably made of heat-resistant inorganic compounds such as alumina, silicon carbide, titanium oxide, silica, magnesia, diatomaceous earth, pumice, zirconium oxide, cerium oxide, calcium sulfate, titanium phosphate, silicon phosphate and their mixtures. Above all, alumina and titanium oxide are advantageously employed. The amount of the active components of the catalyst to be supported varies with types of carriers used, methods of preparing the catalyst, atomic ratios of the active components, etc. and, normally, is not less than 3 weight %, preferably not less than 10 weight %.

As one of typical examples of methods for preparing the catalyst to be used in the present invention, there may be mentioned the procedure of adding oxalic acid to vanadium pentoxide to give a uniform solution, to which an alcohol solution of antimony trichloride is added; then adding an aqueous solution of uranyl nitrate or an aqueous solution of chromium trioxide and adding moldings or powder of a carrier; subsequently evaporating to dryness over a water bath and calcining at a temperature in the region of 500° C.

The catalyst thus obtained shows high activity and selectivity of nitriles.

As alkyl-substituted aromatic compounds which are the starting material of the present invention, use is normally made of alkyl-substituted aromatic compounds in which the substituted alkyl groups have not more than 3 carbon atoms. Included among these are monoalkyl-substituted aromatic compounds such as α,β,γ-picoline, 2-methyl-5-ethylpyridine, toluene, ethylbenzene, n-propylbenzene, cumene, α,β-methylnaphthalene and methylanthracene, dialkyl-substituted aromatic compound such as o-oxylene, p-xylene, m-xylene, o-, m-, p-ethyltoluene, o-, m-, p-isopropyltoluene, o-, m-, p-diethylbenzene, o-, m-, p-diisopropylbenzene, dimethylnaphthalene and dimethylanthracene and lutidines, tri- and more alkyl-substituted aromatic compounds such as mesitylene and collidines and aromatic compounds prepared by substituting hydrogens of aromatic rings of the said compounds by groups not participating in the reaction such as fluorine, chlorine, bromine, nitrile group and nitro group, such as o-, m-, p-chlorotoluene, o-, m-, p-nitrotoluene, o-, m-, p-tolunitrile, and dichlorotoluenes.

As the oxygen-containing gas, use is normally made of air, but oxygen or mixture of oxygen and air, mixture of air and carbon dioxide, mixture of air and steam and mixture of air and nitrogen may be utilized.

The reaction temperature varies greatly with kind and mixing ratios of the starting gas, composition of the catalyst, types of the carrier, etc. and is normally 180° C. to 600° C., preferably 300° to 500° C. The starting gas and catalyst are desirably contacted normally at a space velocity (converted to NTP) in the range of 300 to 3000 ($hr^{-1}$), preferably in the range of 400 to 2000 ($hr^{-1}$). Unreacted alkyl-substituted aromatic compound and ammonia may be recirculated for use in some circumstances.

Referring to the aromatic nitriles obtained according to the method of the present invention, there are produced picolinonitrile from α-picoline, nicotinonitrile from β-picoline, isonicotinonitrile from γ-picoline, and 2,5-dicyanopyridine and nicotinonitrile from 2-methyl-5-ethylpyridine; similarly, there are formed from chlorotoluene the corresponding chlorobenzonitrile, from nitrotoluene the corresponding nitrobenzonitrile, from tolunitrile phthalonitrile, and from dichlorotoluene dichlorobenzonitrile, respectively.

Also, there are produced benzonitrile from toluene, ethylbenzene, n-propylbenzene and cumene; o-tolunitrile, phthalonitrile and phthalimide from o-oxylene, o-isopropyltoluene, o-diethylbenzene and o-diisopropylbenzene; m-tolunitrile and isophthalonitrile from m-xylene, m-isopropyltoluene, m-diethylbenzene and m-diisopropylbenzene; p-tolunitrile and terephthalonitrile from p-xylene, p-isopropyltoluene, p-diethylbenzene and p-diisopropylbenzene; tricyanobenzene, dicyanomonomethylbenzene and monocyanodimethylbenzene and mesitylene; and cyanonaphthalene and phthalonitrile from methylnaphthalene, respectively.

The formed aromatic nitriles are cooled and collected directly as a solid, or are absorbed and collected in a suitable solvent, and can be made the aromatic nitriles with a higher degree of purity by means of some procedure such as distillation, although they are not particularly required to be purified.

The present invention provides the advantages such as;

(1) The objective compound can be obtained in high yields, even when the mixing ratio of ammonia to an alkyl-substituted aromatic compound is reduced to a level in the neighborhood of the stoichiometric ratio (e.g. 1.0 to 1.5 moles of ammonia to 1 mole of an alkyl-substituted aromatic compound), (2) Temperature control in the catalyst bed is easy even at increased concentrations of an alkyl-substituted aromatic compound to air, thus being suited for operation for reaction of the fixed catalyst bed and (3) Not only mono- and dialkyl substituted aromatic compounds but also tri- and more alkyl substituted aromatic compounds such as mesitylene can be led to the corresponding cyano aromatic compounds in high yields.

and permits high-purity aromatic nitriles to be produced economically.

EXAMPLE 1

To a suspension of 65 parts of oxalic acid in 200 parts of water was added 7.85 parts of $V_2O_5$ powder, and the mixture was heated at about 100° C. over a water bath, thus yielding a uniform solution. Then, to the uniform solution were added a solution of 39.4 parts of $SbCl_3$ crystals in 200 parts of ethanol and an aqueous solution of 8.68 parts of $UO_2(NO_3)_2.6H_2O$, and then mixed well. Placed in the mixed solution was 300 parts of fine powder of $Al_2O_3$ calcined at 1300° C., and the alcohol and a part of the water were evaporated over a water bath, while stirring. The resulting paste-formed mixture was wet-molded to a shape of 2 mm diameter $\times$ 5 mm length. The moldings were dried overnight at about 100° C. and calcined at 500° C. for 4 hours in the air, thus yielding a catalyst with V:Sb:U=1:2:0.2 (atomic ratio).

10 ml of the catalyst prepared thus was filled in a flow type fixed bed reactor of 13 mm in diameter having a fluidized heating bath and, while maintaining the reaction bath temperature at 345° C., an ammoxidation was carried out under the conditions of atmospheric pressure and space velocity of 1500 $hr^{-1}$ (converted to NTP) with a mixed gas consisting of 1.0 mole % of β-picoline, 1.1 mole % of ammonia and 97.9 mole % of air, whereby the temperature of the catalyst bed exhibited merely a very limited distribution of maximum 7° C. deviated from the bath temperature, with 99.2 mole % in conversion of β-picoline and 93.9 mole % in yield of nicotinonitrile (based on β-picoline fed).

Also, another reaction was carried out under the same conditions, except for the feeding mixed gas of the changed composition having 1.0 mole % of β-picoline, 2.0% of ammonia and 97.0% of air, whereby there were obtained the results of 99.3 mole % in conversion of β-picoline and 95.7 mole % in nicotinonitrile yield (based on β-picoline fed).

EXAMPLE 2

To a suspension of 65 parts of oxalic acid in 200 parts of water was added 7.85 parts of $V_2O_5$ powder, and the mixture was heated at about 100° C. over a water bath to give a uniform solution. Then, 39.4 parts of $SbCl_3$ crystals was hydrolyzed with about 5000 parts of water, and the mixture was left on standing. The supernatant liquid was decanted and filtration was carried out, followed by washing with about 1000 parts of water to thereby produce $Sb(OH)_3$. The mixed solution consisting of resulted $Sb(OH)_3$, 4.32 parts of $CrO_3$, 5 parts of oxalic acid and 50 parts of water was added to the above uniform solution of $V_2O_5$, and 300 parts of fine powder of $TiO_2$ calcined at 800° C. was placed in the mixture while stirring well. The resulting mixture was stirred well over a water bath to evaporate a part of the water, and was made paste-formed, followed by wet-molding to a shape of 2 mm diameter $\times$ 5 mm length. The moldings were dried at about 100° C. overnight and calcined at 500° C. for 4 hours in the air, thereby yielding a catalyst with V:Sb:Cr=1:2:0.5 (atomic ratio).

10 ml of the catalyst thus prepared was filled in the same reactor as in Example 1 and, while maintaining the reaction bath temperature at 337° C., an ammoxidation was carried out under the conditions of atmospheric pressure and space velocity of 1500 (hr$^{-1}$) with a mixed gas consisting of 1.0 mole % of β-picoline, 1.0 mole % of ammonia and 98 mole % of air, whereby the temperature of the catalyst bed exhibited merely a very limited distribution of maximum 6° C. deviated from the bath temperature, with 100 mole % in conversion of β-picoline and 94.5 mole % in nicotinonitrile yield (based on β-picoline fed).

Also, another reaction was carried out under the same conditions, except for changing the composition of a mixed gas to be fed to that consisting of 1.0 mole % of β-picoline, 3.0% of ammonia and 96.0% of air, whereby the conversion of β-picoline was 100%, with 98.6% in nicotinonitrile yield (based on β-picoline fed).

EXAMPLE 3

To 7.85 parts of $V_2O_5$ were added 65 parts of oxalic acid 200 parts of water, and the mixture was heated at about 100° C. over a water bath to prepare a uniform solution. To the above uniform solution of $V_2O_5$ were added a solution of 39.4 parts of $SbCl_3$ in 200 parts of ethanol and a mixed solution consisting of 3.4 parts of $CrO_3$, 4 parts of oxalic acid and 40 parts of water, and the resulting solution was heated over a water bath. 300 parts of 2-mm spheres of $Al_2O_3$ calcined at 1200° C. was added to the solution, and the water was evaporated over a water bath to thereby impregnate the active components of catalyst on $Al_2O_3$ carrier. There was obtained the catalyst with V:Sb:Cr=1:2:0.4 (atomic ratio) by drying at about 100° C. overnight and calcining at 500° C. for 4 hours in the air.

10 ml of the catalyst thus prepared was filled in the same reactor as in Example 1, and while maintaining the reaction bath temperature at 378° C., an ammoxidation was carried out under the conditions of atmospheric pressure and space velocity of 1500 (hr$^{-1}$) with a mixed gas consisting of 1 mol % of toluene, 3 mol % of ammonia and 96 mol % of air, whereby there were obtained the results of 98.7 mole % in conversion of toluene and 90.1 mole % in benzonitrile yield (based on m-xylene fed).

EXAMPLE 4

In the same manner as in Example 2, except for the use of 59.1 parts of $SbCl_3$ and 8.64 parts of $CrO_3$ in place of 39.4 parts of $SbCl_3$ and 4.32 parts of $CrO_3$ used in Example 2, catalyst preparation was conducted, thereby yielding a catalyst with V:Sb:Cr=1:3:1 (atomic ratio).

In the same reactor as in Example 1, while maintaining the reaction bath temperature at 375° C., an ammoxidation reaction was carried out with a mixed gas consisting of 1.5 mole % of m-xylene, 6 mole % of ammonia and 92.5 mole % of air at a space velocity of 1000 (hr$^{-1}$) (converted to NTP), whereby the temperature of the catalyst bed exhibited merely a very limited distribution of maximum 15° C. deviated from the bath temperature, with 99.8 mole % in conversion of m-xylene and 82.5 mole % in isophthalonitrile yield (based on m-xylene fed).

EXAMPLE 5

By the same procedure as in Example 2, except for the use of 2.59 parts of $CrO_3$ in place of 4.32 parts of $CrO_3$ and wet-molding to a shape of 5 mm diameter×5 mm length, catalyst preparation was conducted, thereby yielding a catalyst with V:Sb:Cr=1:2:0.3 (atomic ratio).

1 l of the catalyst thus prepared was filled in a stainless steel made reaction tube of ¾ inch inner diameter and 3.5 m in length having a niter heating bath jacketed outside and a thermowell of 3 mm outer diameter inserted inside, and a catalyst bed of 2.85 m was produced.

While maintaining the bath temperature for the reaction tube at 378° C., an ammoxidation reaction was carried out by flowing a mixed gas consisting of 1 mole % of m-xylene, 4 mole % of ammonia and 95 mole % of air at a gas inlet pressure of 1.1 kg/cm$^2$ and a spece velocity of 2000 (hr$^{-1}$) (converted to NTP), whereby the conversion of m-xylene was 100 mole %, with the isophthalonitrile yield (based on fed m-xylene) of 83.4 mole %. The temperature of the catalyst bed showed a distribution of maximum 41° C. deviated from the bath temperature.

EXAMPLE 6

By the same procedure as in Example 1, except for the use of 2.17 parts of $UO_2(NO_3)_2.6H_2O$ in place of 8.68 parts of $UO_2(NO_3)_2.6H_2O$, use of a mixture of 150 parts of $Al_2O_3$ fine powder and 150 parts of $TiO_2$ fine powder in place of 300 parts of $Al_2O_3$ fine powder and molding to a shape of 5 mm diameter×5 mm length, catalyst preparation was carried out, thereby yielding a catalyst with V:Sb:U=1:2:0.05 (atomic ratio).

1 l of the catalyst thus prepared was filled in the reactor as employed in Example 5 and, while maintaining the bath for the reaction tube at the temperature of 393° C., an ammoxidation reaction was carried out by flowing a mixed gas consisting of 1.5 mole % of m-xylene, 6 mole % of ammonia and 92.5 mole % of air at a gas inlet pressure of 0.8 kg/cm$^2$ and a space velocity of 1500 (hr$^{-1}$), whereby the conversion of m-xylene was 99.6 mole %, with the isophthalonitrile yield of 80.9 mole % (based on m-xylene fed). The temperature of the catalyst bed exhibited a distribution of maximum 45° C. deviated from the bath temperature, but the reaction temperature remained constant for a prolonged period of time.

EXAMPLE 7

By the same procedure as in Example 3, except for the use of 19.7 parts of $SbCl_3$ in place of 39.4 parts of $SbCl_3$ and 8.65 parts of $CrO_3$ in place of 3.45 parts of $CrO_3$, catalyst preparation was carried out, thereby yielding a catalyst with V:Sb:Cr=1:1:1 (atomic ratio).

10 ml of the catalyst prepared thus was filled in the same reactor as employed in Example 1 and, while maintaining the reaction bath temperature at 420° C., an ammoxidation reaction was carried out by flowing a mixed gas consisting of 1 mole % of mesitylene, 10 mole % of ammonia and 89 mole % of air at atmospheric pressure and a space velocity of 1000 (hr$^{-1}$), whereby the temperature showed a distribution of maximum 21° C. deviated from the bath temperature, with 99.5 mole % in conversion of mesitylene and 68.5 mole % in yield of 1,3,5-tricyanobenzene (based on mesitylene fed).

EXAMPLE 8

By the same procedure as in Example 1, except for the use of 4.34 parts of $UO_2(NO_3)_2.6H_2O$ in place of 8.68 parts of $UO_2(NO_3)_2.6H_2O$ and use of 1.73 parts of $CrO_3$, catalyst preparation was carried out, thereby yielding a catalyst with $V:Sb:Cr:U = 1:2:0.2:0.1$ (atomic ratio). 10 ml of the catalyst prepared thus was filled in the reactor as in Example 1 and, while maintaining the bath temperature at 422° C., an ammoxidation reaction was carried out by flowing a mixed gas consisting of 1 mole % of mesitylene, 8 mole % of ammonia and 91 mole % of air at atmospheric pressure and a space velocity of 1000 ($hr^{-1}$), whereby the temperature of the catalyst bed showed a distribution of maximum 26° C. deviated from the bath temperature, with 99.4 mole % in conversion of mesitylene and 72.0 mole % in yield of 1,3,5-tricyanobenzene (based on mesitylene fed).

EXAMPLE 9

By the same procedure as in Example 3, except for the use of 17.4 parts of $UO_2(NO_3)_2 \cdot 6H_2O$ in place of 3.46 parts of $CrO_3$ and 4 parts of oxalic acid and use of 5 mm spheres of $TiO_2$ in place of 2 mm spheres of $Al_2O_3$, catalyst preparation was carried out, thereby yielding a catalyst with $V:Sb:U = 1:2:0.4$.

1 l of the catalyst prepared thus was filled in the reactor as employed in Example 5 and, while maintaining the bath temperature at 429° C., an ammoxidation reaction was carried out by flowing a mixed gas consisting of 1 mole % of mesitylene, 7 mole % of ammonia and 92 mole % of air at a gas inlet pressure of 0.4 $kg/cm^2$ and a space velocity of 1200 ($hr^{-1}$), whereby the conversion of mesitylene was 100 mole %, with 67.9 mole % of the yield of 1,3,5-tricyanobenzene (based on mesitylene fed). The temperature of the catalyst bed showed a distribution of maximum 31° C. deviated from the bath temperature, but the reaction temperature remained constant for a prolonged period of time.

What is claimed is:

1. A method for producing aromatic nitriles which comprises reacting an alkyl-substituted aromatic compound with ammonia and oxygen in the presence of a catalyst containing, as active ingredients, oxides of (1) vanadium, (2) antimony and (3) at least one of uranium and chromium.

2. A method according to claim 1, wherein the catalyst contains oxides of (1) vanadium, (2) antimony and (3) at least one of uranium and chromium in the atomic ratio of 1:0.1 to 10:0.1 to 5.0.

3. A method according to claim 1, wherein the catalyst contains oxides of (1) vanadium, (2) antimony and (3) at least one of uranium and chromium in the atomic ratio of 1:0.5 to 5:0.01 to 2.0.

4. A method according to claim 1, wherein the catalyst contains oxides of (1) vanadium, (2) antimony and (3) at least one of uranium and chromium in the atomic ratio of 1:1.0 to 3.0:0.02 to 1.0.

5. A method according to claim 1, wherein the reaction is carried out at the temperature ranging from 180° to 600° C.

6. A method according to claim 1, wherein the reaction is carried out at the temperature ranging from 300° to 500° C.

7. A method according to claim 1, wherein the alkyl-substituted aromatic compound is mesitylene.

8. A method according to claim 1, wherein the reaction is carried out in a fixed bed of the catalyst.

9. A method according to claim 1, wherein the catalyst is supported on alumina or titanium oxide.

* * * * *